United States Patent
Yoon et al.

(10) Patent No.: US 6,692,531 B1
(45) Date of Patent: *Feb. 17, 2004

(54) PROSTHETIC STEM WITH CEMENT SLEEVE

(75) Inventors: Yong San Yoon, Taejun (KR); Young Yong Kim, Seoul (KR)

(73) Assignee: Korea Advanced Institute of Science and Technology, Taejun (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,928

(22) Filed: May 11, 2000

(30) Foreign Application Priority Data

Jun. 9, 1999 (KR) .......................................... 1999-21343

(51) Int. Cl.⁷ .................................................. A61F 2/30
(52) U.S. Cl. ................................. 623/23.37; 623/23.46; 623/23.19
(58) Field of Search .......................... 623/20.35, 20.36, 623/22.4, 22.44, 23.11, 23.15, 23.19, 23.2, 23.36, 23.38, 22.43, 23.44, 22.46, 23.25, 23.48, 23.46, 23.37; 606/86, 92

(56) References Cited

U.S. PATENT DOCUMENTS

| | | | | | |
|---|---|---|---|---|---|
| 3,996,625 A | * | 12/1976 | Noiles | ..................... | 623/22.15 |
| 4,283,799 A | * | 8/1981 | Pratt et al. | ................ | 623/23.37 |
| 4,957,510 A | * | 9/1990 | Cremascoli | .............. | 623/22.46 |
| 5,571,204 A | * | 11/1996 | Nies | ......................... | 623/23.19 |
| 5,725,590 A | * | 3/1998 | Maumy et al. | .......... | 623/23.15 |
| 5,766,262 A | * | 6/1998 | Mikhail | .................... | 623/23.25 |
| 6,156,070 A | * | 12/2000 | Incavo et al. | ............ | 623/23.52 |
| 6,214,053 B1 | * | 4/2001 | Ling et al. | ............... | 623/23.11 |
| 6,524,344 B2 | * | 2/2003 | Yoon | ....................... | 623/23.46 |

FOREIGN PATENT DOCUMENTS

KR          85-1814         12/1985

* cited by examiner

Primary Examiner—Bruce Snow
Assistant Examiner—Brian E. Pellegrino
(74) Attorney, Agent, or Firm—Akin Gump Strauss Hauer & Feld, LLP

(57) ABSTRACT

An artificial joint is capable of harmoniously connecting the artificial joint, cement and a bone and facilitating effusion of the cement at the time of implantation, as well as diminishing the stress applied thereto. The artificial joint includes a head, a neck and a stem, the stem being coated in advance with cement so as to easily bond the cement to cement filled in a bone cavity of a human femur. An effusion path for effusing the cement filled in the bone cavity is formed in a longitudinal direction on a surface of the cement coated on the stem so that the cement filled in the bone cavity of the human femur can be easily effused upward through the effusion path when the stem is inserted.

4 Claims, 5 Drawing Sheets

PROSTHETIC STEM WITH CEMENT SLEEVE

TECHNICAL FIELD

The present invention relates to an artificial joint. More particularly, the present invention relates to an artificial joint in which cement filled in a bone cavity of a human femur at the time of implantation can be easily effused upward while the cement mantle might have guaranteed minimal thickness everywhere inside the femur along with correct posture of stem. Any direct contact of the stem with the bone inside femoral canal may evoke early failure of the stem due the passage of the wear material to the bone through the hole in the cement mantle once the debonding of the stem with the cement occurred.

BACKGROUND OF THE INVENTION

In general, an artificial joint includes an acetabulum portion and a femur portion. The femur portion is made of metal or ceramic and the acetabulum portion is made of polyethylene, or both of the femur portion and the acetabulum portion are made of ceramic.

When implanting the cemented artificial hip joint into the human body, the femoral canal should be reamed and cleaned. After filling cement in, a stem of the artificial joint should be inserted in such correct posture that the cement mantle should cover the stem completely with uniform thickness inside the femur.

At that time, the cement for fixing the human femur and the stem of the artificial joint has not a chemical fixation power and the fixation of the human femur and the stem of the artificial joint are accomplished by means of merely physical bonding.

The conventional artificial joint implanted as above described is disclosed in Korean Patent Publication No.85-1814, filed by and permitted to the present applicant, and will be explained with reference to FIG. 1.

The artificial joint is composed of a head 2, a neck 3, a collar 4 and a stem 5 from the upper portion, incorporated together. The edge of the collar 4 is curved to adhere closely to an upper end of a cortical bone of the human femur. An upper cross section of the stem 5 is an ellipse shape close to a circle and toward below, the cross section of the stem 5 becomes more close to a circle. This shape of the stem 5 can prevent a torsion due to a perpendicular pressure applied from the upper of the stem and a horizontal force applied to the stem.

A wing 7 with a suitable thickness is protruded in a longitudinal direction on an upper-outer surface of the stem 5 so that it can prevent the artificial joint from rotating in the human femur due to a torque in any direction. A center of the wing 7 is formed with a fixing hole 8 for fixing the wing 7 to the human femur.

A plurality of steel wire holes 7 with a suitable pitch are formed in the longitudinal direction of the stem 5 in an inner side of the wing 7, and a chain type of steel wires 10 are inserted into the steel wire holes 9 and wind the surface of the stem 5. The whole surface of the stem 5 including a portion wound with the steel wires 10 is coated with cement 6 having a suitable thickness. This coating of the cement can facilitate the bonding of the cement coated on the whole surface of the stem 5 and the cement filled in the human femur and can decrease an amount of cement used in implantation to diminish an amount of heat generated in curing.

When implanting the aforementioned artificial joint into the femur of human body, femoral cavity should be enlarged by reaming so that the stem 5 of the artificial joint 1 can be inserted into the bone cavity of the human femur along with suitable amount of cement being filled in the bone cavity of the human femur. Thus, the stem 5 is inserted into the bone cavity of the human femur filled with the cement. The cement filled in the bone cavity of the human femur is bonded to the cement 6 coated in advance on the surface of the stem 5, thereby fixedly adhering the stem 5 to the human femur.

When implanting the conventional artificial joint into the human body, as the stem 5 is inserted, the cement filled in the femoral cavity of the human femur should be effused along the surface of the stem 5 and adhered to the cement coated in advance of the surface of the stem 5. However, there is no effusion path for effusing the cement filled in the bone cavity of the human femur, so that the effusion of the cement filled in the bone cavity is not easy. The cement filled in the bone cavity of the human femur is adhered to the smooth surface of the cement 6 coated in advance on the surface of the stem 5 and thus, the adhesion power is small.

The conventional artificial joint has not an absorbing means for absorbing stress concentrated in the cement in the activity of the human body, so that a large load is applied to the stem of the artificial joint to shorten a lifetime of the artificial joint.

SUMMARY OF THE INVENTION

Therefore, the present invention is made in order to solve the aforementioned problems. An object of the present invention is to provide an artificial joint capable of facilitating the effusion of cement during implantation of the artificial joint and firmly bond the artificial joint with the human femur along with complete encapsulation of stem with cement inside the femoral canal.

Another object of the present invention is to provide an artificial joint capable of reducing stress applied to the cement.

The above objects can be accomplished by an artificial joint including a head, a neck and a stem and being implanted into a bone cavity of a human femur, said stem coated in advance with cement so as to easily bond the cement to cement used at the time of implantation and to diminish quantity of heat generated when cured, wherein a effusion path is formed in a longitudinal direction on a surface of the cement coated on said stem, so that the cement filled in the bone cavity can be easily effused upward through said effusion path when said stem is inserted into the bone cavity. Complete encapsulation of stem with cement inside the femoral canal is also a strong benefit of precoating. Any direct contact of stem with bone will provide a path for the wear particle to the bone causing osteolysis at the site.

It is preferable that a slot for absorbing stress is further formed in an upper portion of said stem.

It is more preferable that said slot has a slope of 20° with respect to the surface of said stem.

Preferably, an inner end of said slot has a spherical shape so that cracks due to concentration of the stress should not be generated.

More preferably, said effusion path is made of one or more grooves with a saw-toothed cross section.

It is still more preferable that said effusion path is formed on the entire surface of the cement coated on said stem or on predetermined positions of the surface of the cement coated on said stem.

Also, the above objects are accomplished by an artificial joint including a head, a neck and a stem and being implanted into a bone cavity of a human femur, said stem coated in advance with cement so as to easily bond the cement to cement used at the time of implantation and to diminish quantity of heat generated when cured, wherein a slot for absorbing stress is further formed in an upper portion of said stem.

It is preferable that said slot has a slope of 20° with respect to the surface of said stem.

More preferably, an inner end of said slot has a spherical shape so that cracks due to concentration of the stress should not be generated.

BRIEF DESCRIPTION OF THE DRAWINGS

The embodiments of the present invention will be explained with reference to the accompanying drawings, in which.

DETAILED DESCRIPTION OF THE INVENTION

The above objects, other objects, features and advantages of the present invention will be better understood from the following description taken in conjunction with the drawings.

Figure 1:
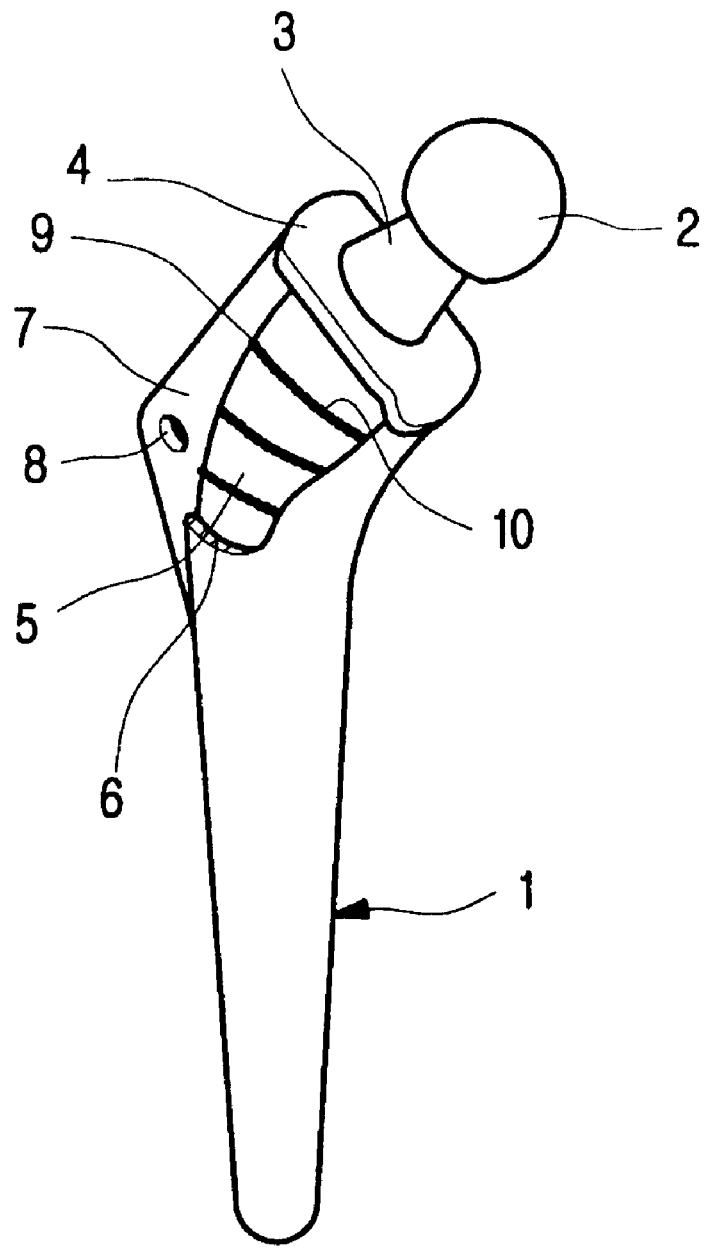
FIG. 1 is a perspective view of a conventional artificial joint.
Figure 2:
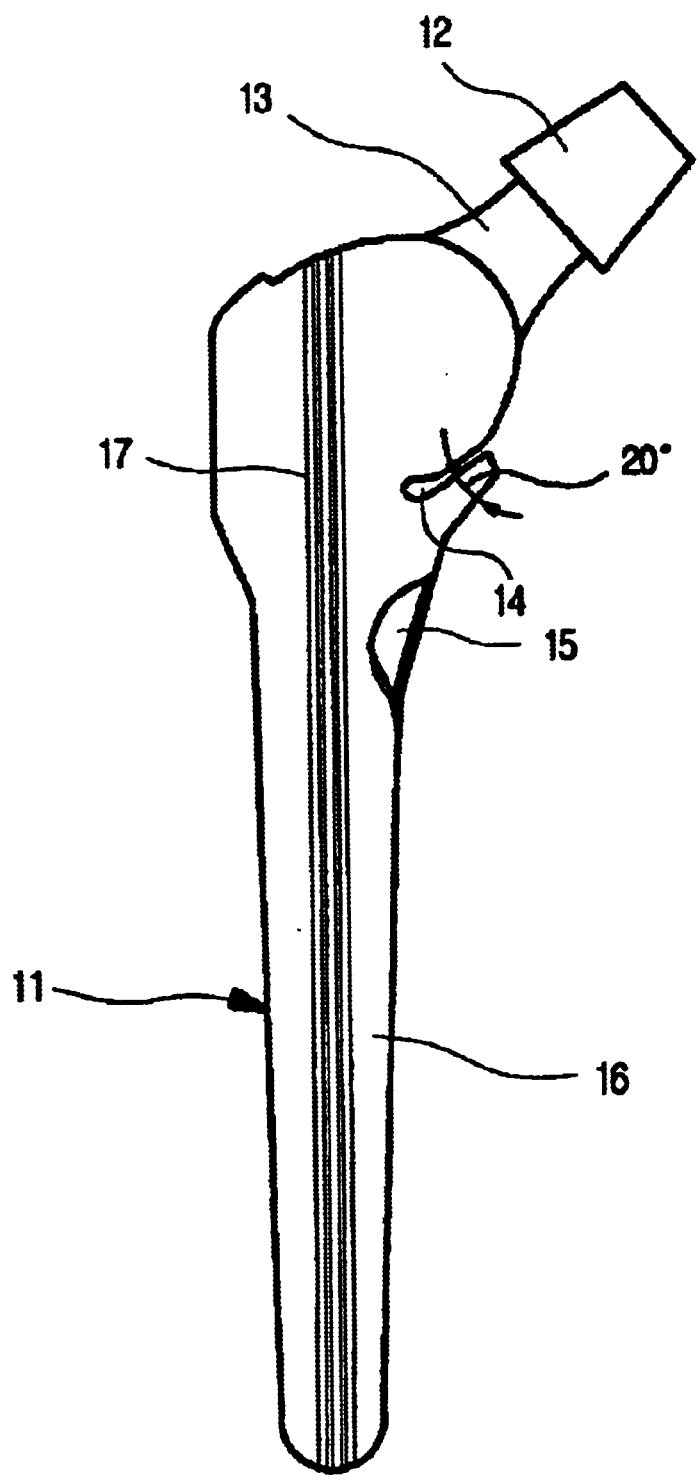
FIG. 2 is a side view of an artificial joint according to an embodiment of the present invention.
Figure 3:
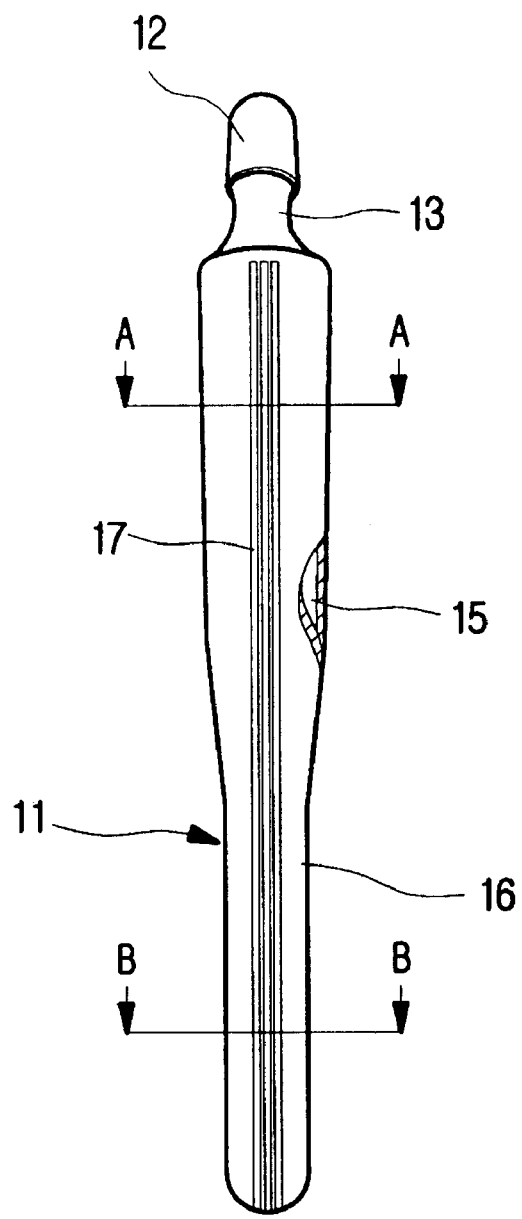
FIG. 3 is a backside view of the artificial joint shown in FIG. 2.
Figure 4:
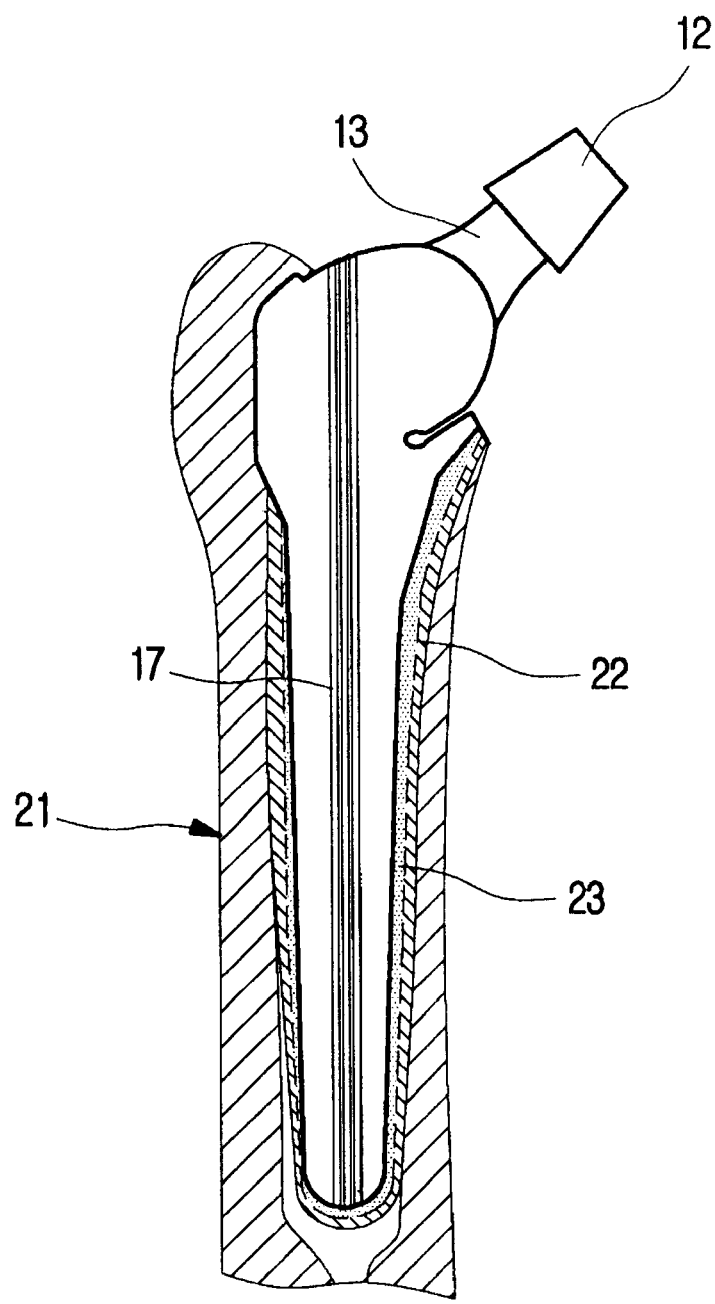
FIG. 4 is a cross-sectional view for illustrating a state of implanting the artificial joint shown in FIG. 2 into a human femur.
Figure 5:
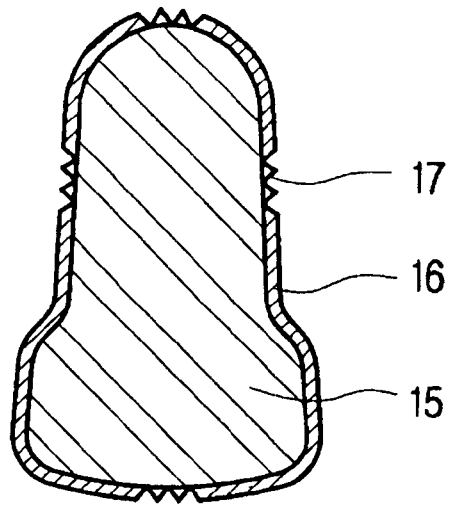
FIG. 5 is a cross-sectional view of the artificial joint according to the present invention taken along a line A—A of FIG. 3.
Figure 6:
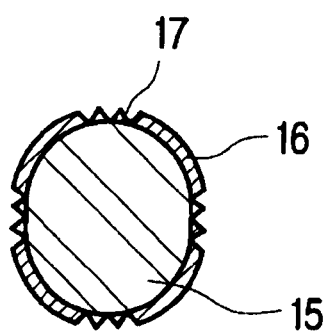
FIG. 6 is a cross-sectional view of the artificial joint according to the present invention taken along a line B—B of FIG. 3.

FIG. 2 and FIG. 3 are a side view and a backside view of an artificial joint according to an embodiment of the present invention, respectively, FIG. 4 is a cross-sectional view for illustrating a state of implanting the artificial joint shown in FIG. 2 into a femur of a human body and FIG. 5 and FIG. 6 are cross-sectional views of the artificial joint taken lines A—A and B—B of FIG. 3, respectively.

As shown in FIG. 2 and FIG. 3, the artificial joint 11 according to the present invention includes of a head 12, a neck 13 and a stem 15 from the upper portion to be incorporated together.

An upper portion of the stem 15, as shown in FIG. 5, is formed to have a cross section of which a backside is wider than a front side thereof. That is, the upper portion of the stem 15 has a mediate shape of a cross section between a rectangular and an ellipse. This cross-sectional shape of the upper portion of the stem 15 can prevent a rotation of the artificial joint due to a rotary torque in any direction after implantation of the artificial joint. A lower portion of the stem 15, as shown in FIG. 6, is formed to have a circular cross section. That is, in the cross section of the stem 15, the upper portion has a mediate shape between a rectangular and an ellipse, and, toward a lower end, has a shape close to a circle. This shape of the stem 15 can prevent a torsion due to a perpendicular pressure applied from the upper of the stem 15 and a horizontal force applied to the stem 15.

A slot 14 for reducing stress concentrated on the cement during activity of a human body is formed in a front-upper portion of the stem 15. When the stress is applied to the cement during activity of a human body, the slot 14 provides a space in which a part of the stem 15 can move elastically. This slot 14 is formed to have a slope of 20° with respect to the surface of the stem 15 and an inner end of the slot 14 is formed to have a spherical shape so that cracks due to concentration of the stress should not be generated.

The surface of the stem 15 is coated with cement 16 having a suitable thickness. This coating of the cement 16 can facilitate the bonding of the cement 16 coated on the whole surface of the stem 5 and cement filled in the human femur and reduce the amount of cement used in implantation and heat generated in curing as well as guaranteed complete encapsulation of cement mantle.

A surface of the cement 16 coated so is formed with an effusion path 17 along which the cement filled in advance in a bone cavity of the human femur can be effused upward in implantation of the artificial joint. The effusion path 17 includes one or more grooves with a saw-toothed cross section. The grooves are formed in a longitudinal direction of the stem 15. Four sets of grooves can be formed in a predetermined pitch on a surface of the cement coated on the stem 15, in which a set of grooves is made of several grooves. Of course, the grooves may be formed on the whole surface of the cement coated on the stem 15 and four and more or less sets of grooves may be formed. Formation of the effusion path 17 causes the exposed surface area of the cement 16 large and help to make good bonding with the outer cement.

When implanting the artificial joint 11 of the present invention into a femur 21 of a human body, as shown in FIG. 4, a space 22 in the bone cavity of the human femur 21 is reamed out so that the stem 15 with precoated cement layer 23 of the artificial joint 11 can be inserted into the bone cavity of the human femur 21 and then, a suitable amount of cement is filled into the bone cavity 22 of the human femur 21. Then, the stem 15 with cement precoating 23 is inserted into the bone cavity 22 of the human femur 21 filled with the cement 22. The cement 22 filled in the bone cavity 22 of the human femur 21 is effused along the effusion path 17 formed on the surface of the cement 23 coated in advance on the stem 15 and is bonded with the cement 23 coated in advance on the surface of the stem 15, thereby fixedly adhering the stem 15 to the human femur 21 to be incorporated together.

As described above in detail, since the artificial joint of the present invention is coupled to the human femur with the cement filled in the human femur effused along the effusion path formed on the cement coated on the stem, the implantation becomes easy. Because of increasing in the fixing area due to the effusion path, the fixing power is great.

Also, since the slot for absorbing and diminishing the stress applied to the cement during activity of a human body is formed, the lifetime of the artificial joint according to the present invention can be elongated.

Although representative embodiments of the artificial joint according to the present invention have been disclosed for illustrative purposes with reference to the appended drawings, the present invention should not be limited to the embodiments. Those who are skilled in the art will appreciate that various modifications, additions and substitutions are possible without departing from the scope and spirit of the present invention as defined in the accompanying claims and the equivalents thereof.

What is claimed is:

1. An artificial joint for implantation into a bone canal of a human femur, wherein the bone canal is filled with cement, the joint comprising:

a pin-shaped head portion for insertion into an articulating ball, a stem portion comprising a longitudinal axis and an insertion part inserted into the bone canal; and a neck portion connecting the head portion and the stem portion, wherein the insertion part of the stem portion comprises a smooth surface at least a part of which is coated with a cement layer having an outer surface, and a plurality of grooves formed on at least one predetermined position of the outer surface of the cement layer in a direction of the longitudinal axis, each groove having a saw-toothed cross section, and wherein the artificial joint may firmly bond with cement filled in the bone canal, the stem portion may be tightly encapsulated with the cement filled in the bone canal, and cement filled in the bone canal may be effused when the stem portion is inserted into the bone canal.

2. The artificial joint in accordance with claim 1, further comprising a slot formed in the stem portion near the head portion for absorbing stress in the joint.

3. The artificial joint in accordance with claim 2, wherein the slot comprises an inner end having a spherical shape for preventing generation of cracks due to concentration of the stress in the joint.

4. The artificial joint in accordance with claim 1, wherein the plurality of grooves are formed on the entire outer surface of the cement layer.

* * * * *